United States Patent [19]

Scott et al.

[11] Patent Number: 5,187,089
[45] Date of Patent: Feb. 16, 1993

[54] PROTEASE NEXIN-I VARIANTS WHICH INHIBIT ELASTASE

[75] Inventors: Randy W. Scott, Sunnyvale; Fred Golini, San Mateo; Michael McGrogan, San Carlos, all of Calif.

[73] Assignee: Incyte Pharmaceuticals, Inc., Palo Alto, Calif.

[21] Appl. No.: 542,484

[22] Filed: Jun. 21, 1990

[51] Int. Cl.$^5$ .......................... C12N 9/48; C12N 9/66
[52] U.S. Cl. ..................................... 435/212; 435/218
[58] Field of Search ............... 435/218, 212, 184, 69.2; 530/350

[56] References Cited

FOREIGN PATENT DOCUMENTS 0251505 1/1988 European Pat. Off. .

OTHER PUBLICATIONS

Lehninger, *Biochemistry*, Worth Publishers, 1975, pp. 72-75.
McGrogan et al. Bio/technology 1988, vol. 6, 172-177.
Baker et al. (1987) UCLA Symposia, Series V, vol. 65 307-323.
Courtney et al. (1985) Nature 313, 149-151.
Bieth *Bull. Euro. physiolpath. Resp.* (1980) 16:183-195.
Scott et al., *J. Biol. Chem.* (1985) 260(11):7029-7034.
Scott et al., *J. Biol. Chem.* (1983) 58:10439-10444.
Eaton et al., *J. Biol. Chem.* (1984) 259(10):6241-6247.

*Primary Examiner*—Elizabeth C. Wehmar
*Assistant Examiner*—Deborah Crouch
*Attorney, Agent, or Firm*—Morrison & Foerster

[57] ABSTRACT

One or more amino acid residues within the reactive site region of protease nexin-I are altered in order to create analogs or variants or protease nexin-I. These analogs have substantially different protease specificities as well as different effects on regulating the activity of proteolytic enzymes which enzymes have substantial effects on a number of different physiological functions. Formulations containing the protease nexin-I variants and methods for administering these formulations to obtain desirable therapeutic results are disclosed.

4 Claims, 5 Drawing Sheets

SEQUENCE OF PROTEASE NEXIN I TYPE ALPHA

```
CTGTGACCCTTCCTCGCCGCCGCCGCTTCGCCTCCTCCTCCGACTCCCCGCCGCCGAGACTAGGCTCCGCCTCCGCCTCCGGTTGCGGGACCCCTCCGGCCGCCCCTGGGATCCAGCGAGCG

S1                                                                            1
CGGTCGTCCTTGGTGGAAGGAACC                 ATG AAC TGG CAT CTC CCC CTC CTC TTC GCC TCT GTG ACG CTG CCT TCC ATC TGC TCC CAC TTC AAT
                                         Met Asn Trp His Leu Pro Leu Leu Phe Ala Ser Val Thr Leu Pro Ser Ile Cys Ser His Phe Asn

10                                              S10                       20                                 30
CCT CTG TCT CTC GAG GAA CTA GGC CTC AAC ACG GGG ATC CAG GTT TTC AAT CAG ATT GTG AAG TCG AGG CCT CAT GAC AAC ATC GTG ATC
Pro Leu Ser Leu Glu Glu Leu Gly Leu Asn Thr Gly Ile Gln Val Phe Asn Gln Ile Val Lys Ser Arg Pro His Asp Asn Ile Val Ile 40                              50                                  60
TCT CCC CAT GGG ATT GCC TCG GTC CTG GGG ATG CTT CAG CTG GGA GAC GGC AGG ACC AAG CAG CTC GCC ATG GTG ATG AGA TAC
Ser Pro His Gly Ile Ala Ser Val Leu Gly Met Leu Gln Leu Gly Asp Gly Arg Thr Lys Gln Leu Ala Met Val Met Arg Tyr 70                              80                                  90
GGC GTA AAT GGA GTT GGT AAA ATA TTA AAG ATC AAC AAG GCC ATC GTG TCC AAG AAT AAG AAA AAT GTG ACA GTG GCT AAC GCC
Gly Val Asn Gly Val Gly Lys Ile Leu Lys Ile Asn Lys Ala Ile Val Ser Lys Asn Lys Lys Asn Val Thr Val Ala Asn Ala 100                             110                                 120
GTG TTT GTT AAG AAT GCC TCT GAA ATT GAA GTG CCT TTT GTT ACA AGG AAC AAA GAT GTG TTC AGG TGT GAG GTC CGG AAT GTG
Val Phe Val Lys Asn Ala Ser Glu Ile Glu Val Pro Phe Val Thr Arg Asn Lys Asp Val Phe Arg Cys Glu Val Arg Asn Val 130                             140                                 150
GAG GAT CCA GCC TCT GCC TGT GAT TCC ATC AAT GCA TGG GTT AAA GAA ACC AGG GAT ATT GAA ACC AAT CTG CTG TCC CCA
Glu Asp Pro Ala Ser Ala Cys Asp Ser Ile Asn Ala Trp Val Lys Glu Thr Arg Asp Ile Glu Thr Asn Leu Leu Ser Pro 160                             170                                 180
AGA GGT GTG CTC ACC AGA CTG GTC CTC GTC AAC GCA GTG TAT TTC AAG GGT CTG TGG AAA TCA CGG TTC CAA GAG AAC ACA
Arg Gly Val Leu Thr Arg Leu Val Leu Val Asn Ala Val Tyr Phe Lys Gly Leu Trp Lys Ser Arg Phe Gln Glu Asn Thr 190                             200                                 210       Sal1
ATT GAT GGT GTG CTC AGA GTG ACT TTC ATC TAT CAA GTG CCA ATG AAG TCA GCT CTC CGG TTC CGG TGT GGG TCG ACA AGT GCC
Ile Asp Gly Val Leu Arg Val Thr Phe Ile Tyr Gln Val Pro Met Lys Ser Ala Leu Arg Phe Arg Cys Gly Ser Thr Ser Ala

Bgl II
         220                             230                                 240       SacI
AAA CGC ACT TTC GTG GCA GCC GAC GGG AAA TCC TAT CAG CTG CCA CGG TTC CGG TGT GGG            GAG AGC TCC ACT
Lys Arg Thr Phe Val Ala Ala Asp Gly Lys Ser Tyr Gln Leu Pro Arg Phe Arg Cys Gly            Glu Ser Ser Thr

CCC AAT GAT TTA TGG TAC AAC TTC ATT GAA GCC CTG CTG ATT GCA CCG ATT GCG
Pro Asn Asp Leu Trp Tyr Asn Phe Ile Glu Leu Leu Ile Ala Pro Leu Ala
```

FIG. 1-1

```
CCG CTG TCT GCC ATC ATC CCA CAC ATC AGC ACC AAG ACC ATA GAC AGC TGG ATG AGC ATC ATG GTG CCC AAG AGG GTG CAG GTG ATC CTG
Pro Leu Ser Ala Ile Ile Pro His Ile Ser Thr Lys Thr Ile Asp Ser Trp Met Ser Ile Met Val Pro Lys Arg Val Gln Val Ile Leu
                        250                             260                             270                     300
CCC AAG TTC ACA GCT GTA GCA CAA ACA GAT TTG AAG GAG CCG CTG ATT CTT GGC ATT ACT GAC ATG TTT GAT TCA AAG GCA AAT
Pro Lys Phe Thr Ala Val Ala Gln Thr Asp Leu Lys Glu Pro Leu Ile Leu Gly Ile Thr Asp Met Phe Asp Ser Lys Ala Asn
            280                             290                                         300
                                                                                                                HindIII
TTT GCA AAA ATA ACA AGG TCA GAA AAC CTC CAT GTT TCT CAT ATC TTG CAA AAA GCA AAA ATT GAA GTC AGT GAT GGA ACC AAA GCT
Phe Ala Lys Ile Thr Arg Ser Glu Asn Leu His Val Ser His Ile Leu Gln Lys Ala Lys Ile Glu Val Ser Asp Gly Thr Lys Ala
            310                             320                             330
                                345 346
TCA GCA GCA ACT GCA ATT CTC ATT GCA ACT GCA AGA CCT TTT CTG TTT ATC CGA CAT AAT
Ser Ala Ala Thr Ala Ile Leu Ile Ala Arg Ser Pro Pro Trp Pro Phe Ile Val Asp Arg Pro Phe Leu Phe Ile Arg His Asn
            340                             350                             360
                        378
CCT ACA-GGT GCT GTG TTA TTC ATG GGG CAG ATA AAC AAA CCC TGA AGAGTATACAAAGAAGAAACCATGCAAAGCAACGACTACTTGCTACGAAGAAAGACTCCT
Pro Thr Gly Ala Val Leu Phe Met Gly Gln Ile Asn Lys Pro ---
            370
TTCCTGCATCTTCTGTAAATATTCTTGTACATCGCATTCTTTTTCAAAACGTAGTTCTTAGGAAGCAGACTCGATGCAACTGTTCCTGTTCTGGGAGGTATTGGAGGGAAAAACA
AGCAGGATGCCTGGCACAGTGCCTGTACTGAGGATTGATATAGAAAGACTTCCAGATGCCTAAACTACTGAACTGTTACCTAGGTTAACATCCCTGTTGAGGTATTTGCT
GTTGTCCAGTTAGGAATTTTGTTTGTTTGCTCTATATGTGCGGCTTTTCAGAAGAAATTAATCAGTGTGACAGAAAAAAATGTTTATGGTAGCTTTTACTTTTTATGAAA
AAAAATTATTGTTCCTTTAAATTCTTTTCCCCATCCCCCTCCAAAGTCTTGATAGCAAGCGGTTATTTTGGGGTAGAAACGGTGAAATCTCTAGCCTCT I I GTGTTTTGTGTT
GTGTTGTGTTGTGTTTATATAATGCATGTATTCACTAAAAAACGTCCTGTCTTGCTAGACAAGGTTGTGCATGTGCCTGTCACTGAGTCTGTCTACCTATGGA
TTTGCATTTTGTATTTGTACAAGTAAAAATAACT
```

FIG. I-2

SEQUENCE OF PROTEASE NEXIN I TYPE BETA

```
CTGTGACCCTCCTCGCGCGCCGCTTCGCTCCTCCGACTCCCCGCCGAGACTAGGCTCCGCTCCGGTTGCGGGGACCCCTCGGGCCCCCTGGGGATCCAGCGAGCG

S1                                                                              1
CGGTCGTCCTTGGTGGAAGGAACC ATG AAC TGG CAT CTC CCC CTC TTC GCC TCT GTG ACG CTG CCT TCC ATC TGC TCC CAC TTC AAT
                         Met Asn Trp His Leu Pro Leu Phe Ala Ser Val Thr Leu Pro Ser Ile Cys Ser His Phe Asn
            10                              S10                         20                          30
CCT CTG TCT CTC GAG GAA CTA GGC TCC AAC ACG GTT TTC AAT CAG ATT GTG AAG TCG AGG CCT CAT GAC AAC ATC GTG ATC
Pro Leu Ser Leu Glu Glu Leu Gly Ser Asn Thr Val Phe Asn Gln Ile Val Lys Ser Arg Pro His Asp Asn Ile Val Ile
            40                              50                          60
TCT CCC CAT GGG ATT GCC TCG GTC CTG CTT CAG CTG GGG ATG CTT GGG GAC GGC GAC CTC GCC ATG GTG ATG AGA TAC
Ser Pro His Gly Ile Ala Ser Val Leu Leu Gln Leu Gly Met Leu Gly Ala Asp Gly Leu Ala Met Val Met Arg Tyr
            70                              80                          90
GGC GTA AAT GGA GTT GGT AAA ATA TTA AAG AAG ATC AAC AAG GCC ATC GTC TCC AAG AAA AAT CAG ATT GTG GCT AAC GCC
Gly Val Asn Gly Val Gly Lys Ile Leu Lys Lys Ile Asn Lys Ala Ile Val Ser Lys Lys Asn Gln Ile Val Ala Asn Ala
            100                             110                         120
GTG TTT GTT AAG AAT GCC TCT GAA ATT GAA GTG CCT TTT GTT ACA AGG AAC AAA GAT GTG TTC CAG TGT GAG GTC CGG AAT GTG AAC TTT
Val Phe Val Lys Asn Ala Ser Glu Ile Glu Val Pro Phe Val Thr Arg Asn Lys Asp Val Phe Gln Cys Glu Val Arg Asn Val Asn Phe
            130                             140                         150                                 BglII
GAG GAT CCA CCA TCT GCC TGT GAT TCC ATC AAT GCA TGG GTT AAA GAA ACC ACC AGG GAT ATT ATT GAC AAT CTG CTG TCC CCA GAT CTT
Glu Asp Pro Pro Ser Ala Cys Asp Ser Ile Asn Ala Trp Val Lys Glu Thr Thr Arg Asp Ile Ile Asp Asn Leu Leu Ser Pro Asp Leu
            160                             170                         180
ATT GAT GGT GTG CTC ACC AGA CTG GTC CTC GTC AAC GCA GTG TAT TTC AAG GGT CTG TGG AAG TCA CGG TTC CAA CCC GAG AAC ACA AAG
Ile Asp Gly Val Leu Thr Arg Leu Val Leu Val Asn Ala Val Tyr Phe Lys Gly Leu Trp Lys Ser Arg Phe Gln Pro Glu Asn Thr Lys
            190                             200                         210                 SalI
AAA CGC ACT TTC GTG GCA GCC GAC GGG AAA TCC TAT CAA GTG CCA ATG CTG GCC CAG CTC TCC GTG TTC CGG TTT GGG TCG ACA AGT GCC
Lys Arg Thr Phe Val Ala Ala Asp Gly Lys Ser Tyr Gln Val Pro Met Leu Ala Gln Leu Ser Val Phe Arg Phe Gly Ser Thr Ser Ala
            220                             230                         240                 SacI
CCC AAT GAT TTA TGG TAC AAC TTC ATT GAA CCC CTA CAC GGG GAA AGC AGC ATG CTG ATT GCA CTG CCG ACT AGC TCC ACT
Pro Asn Asp Leu Trp Tyr Asn Phe Ile Glu Pro Leu His Gly Glu Ser Ser Met Leu Ile Ala Leu Pro Thr Ser Ser Thr
```

FIG.2-1

```
CCG CTG TCT GCC ATC ATC CCA CAC ATC AGC ACC AAG ACC ATA GAC AGC TGG ATG AGC ATC ATG GTG CCC AAG AGG GTG CAG GTG ATC CTG
Pro Leu Ser Ala Ile Ile Pro His Ile Ser Thr Lys Thr Ile Asp Ser Trp Met Ser Ile Met Val Pro Lys Arg Val Gln Val Ile Leu
                    250                             260                             270

CCC AAG TTC ACA GCT GTA GCA CAA ACA GAT TTG AAG GAG CCG CTG AAA GTT CTT GGC ATT ACT GAC ATG TTT GAT TCA AAG GCA AAT
Pro Lys Phe Thr Ala Val Ala Gln Thr Asp Leu Lys Glu Pro Leu Lys Val Leu Gly Ile Thr Asp Met Phe Asp Ser Lys Ala Asn
            280                             290                             300
                                                                                                        HindIII
TTT GCA AAA ATA ACA ACA GGG TCA GAA AAC CTC CAT GTT TCT CAT ATC TTG CAA AAA GCA ATT GAA GTC AGT GAT GGA ACC AAA
Phe Ala Lys Ile Thr Thr Gly Ser Glu Asn Leu His Val Ser His Ile Leu Gln Lys Ala Ile Glu Val Ser Asp Gly Thr Lys
                    310                             320                             330

GCT TCA GCA ACA GCA ATT CTC ATT GCA AGA TCA TCG CCT TGG TTT ATA GTA GAC AGA CCT TTC CTG TTC ATC CGA CAT
Ala Ser Ala Thr Ala Ile Leu Ile Ala Arg Ser Ser Pro Trp Phe Ile Val Asp Arg Pro Phe Leu Phe Ile Arg His
                340             346 347         350                             360

AAT CCT ACA GGT GTG TTA TTC ATG GGG CAG ATA AAC CCC TGA AGAGTATACAAAAGAAACCATGCAAAGCAACTGATGCAACTGTTCCTGTCTCGGGAGGTATTGGAGGAAAAA
Asn Pro Thr Gly Val Leu Phe Met Gly Gln Ile Asn Lys Pro ---
                370                         378
CCTTCCTGCATCTTTCTGTAAATATTCTTGTACATCGCATTCTTTTCAAAACGTAGTTTCTTAGGAAGCAGACTCGATGCAACTGTTCCTGTCTCGGGAGGTATTGGAGGAAAAA
ACAAGCAGGATGCCTGGCACAGTGCTACTGAGGATTGATATAGAAAGACTTCCAGATGCCTAAAGACTTCCAGATGCCTAAAGACTTGTGACAGAAAAAAATGTTTATGGTAGCTTTTACTTTTTATG
GCTGTTTGTCCAGTTAGGAATTTTGTTTTGTTTGCTCTATATGTGCGGCTTTCAGAAGACTTGTGGGCTTTCAGAAGTCTTGATAGCAAGCGGTATTTGGGGGTAGAAACGGTGAAATCTCTAGCCTCTTTGTGTTTTGTT
AAAAAAAATTATTTGTTCCTTTAAATTCTTTTCCCCATCCTTTAAATTCACTAAATAAAATTTAAAAAACGTCCTGCTCTTGCTAGACAAGGTTGTGCATGTGCCTGTCTCACTACTGAGTCGTCGTCTCTACCTAT
GTTGTTGTTGTTGTGTTTATATAATGCATGTATTCACTAAATAAAATTTAAAAAACGTCCTGCTCTTGCTAGACAAGGTTGTGCATGTGCCTGTCTCACTACTGAGTCGTCGTCTCTACCTAT
GGATTTGCATTTTTGTATTTTGTACAAAGTAAAATAACT
```

FIG. 2-2

CHARACTERIZATION OF RECOMBINANT PN-I VARIANTS

| Expression System | Variant | Description | Rate Association Constant | | | | |
|---|---|---|---|---|---|---|---|
| | | | Thrombin heparin + | Thrombin heparin - | Urokinase | tPA | Elastase heparin - | Elastase heparin + |
| Fibroblast (native) | PN-I | native | 1.2 E+08 | 6.0 E+5 | 1.5 E+05 | 3.0 E+04 | No Activity |
| CHO | PN-I alpha | native | 7.7 E+07 | 1.7 E+6 | | | |
| | PN-I beta | native | 7.7 E+07 | 1.8 E+6 | | | |
| Baculovirus | PN-I alpha | native | 9.0 E+07 | 1.8 E+6 | 2.0 E+05 | 3.2 E+04 | |
| | PN-I beta | native | 1.0 E+08 | 2.2 E+6 | | | |
| | Variant #1 | Thr 346 | 5.0 E+07 | 1.8 E+6 | 2.0 E+05 | | |
| | Variant #2 | Met 346 | 5.0 E+06 | 2.2 E+5 | | 8.5 E+04 | |
| | Variant #3 | Val 345 | No Activity | No Activity | | | 6.2 E+05 | >6.0 E+07 |

FIG. 3

PROTEASE NEXIN-I VARIANTS WHICH INHIBIT ELASTASE

FIELD OF THE INVENTION

This invention relates generally to the field of proteolytic enzymes and the inhibition of their activity. More specifically, this invention relates to serine protease inhibitors which are variants of protease nexin-I and to pharmaceutical compositions containing these variants and their use.

BACKGROUND OF THE INVENTION

Many natural physiological functions such as tissue remodeling, inflammation, coagulation, and fibrinolysis require proteolytic enzymes. Of particular importance is a mechanistic class of proteases called serine proteases. The active site of all functional members of the serine protease family contains a characteristic catalytic triad consisting of serine (hence the name), aspartic acid and histidine. The hydroxyl group of the catalytic site serine is involved in a nucleophilic attack on the carbonyl carbon of the peptide bond to be hydrolyzed resulting in acylation of the protease and hydrolysis of the peptide bond. This is followed rapidly by a deacylation step resulting in the release of intact protease.

Although originally named for their mechanism of action, members of the serine protease family also show significant sequence and structural homology. Some serine proteases are very specific, cleaving only certain peptide bonds of a specific target protein while others are very nonspecific, degrading multiple target proteins into small peptides.

Serine proteases are regulated at many levels. Some are synthesized as inactive proenzymes and are activated only during specific events and at specific locations. This allows the body to respond rapidly to a physiological perturbation by activating an already present reservoir of proteolytic activity. Coagulation, for example, is carried out when circulating proenzymes such as factor X and prothrombin are sequentially activated in response to injury resulting in a cascade of clotting activity. In addition, proteolytic activity is often localized to specific sites, such as receptor binding sites which can cause high local concentrations of protease or proenzyme ready for activation.

Once activated, it is extremely important that proteolytic activity be confined both spatially and temporally. This control is often achieved by the presence of specific inhibitors which block proteolytic activity. An important family of related proteins, the serine protease inhibitors, or "serpins", are key in the regulation of serine proteases. Like the serine proteases, serpins were first defined by their common mechanism of action but later turned out to be highly homologous both in terms of sequence and structure.

Serpins all contain an inhibitor domain with a reactive peptide bond defined on either side by the $P_1$ and $P_1'$ in a direction to the left away from the reactive site, the amino acids are referred to as $P_1$, $P_2$, $P_3$, etc., and in a direction to the right away from the reactive site they are referred to as $P_1'$, $P_2'$, $P_3'$, etc. The $P_1$ residue is recognized by the substrate binding pocket of the target protease which attacks the reactive peptide bond as though a normal substrate. However, hydrolysis of the peptide bond and release of the protease does not proceed to completion. The normal deacylation step is so slow that the reaction becomes essentially irreversible and the protease becomes trapped in a stable, equimolar complex.

Protease nexin-I (PN-I) is a member of the serpin family. PN-I is produced by many different cell types including fibroblasts, glial cells, and platelets. PN-I is secreted by cells into the extracellular environment where it binds to and inhibits target serine proteases. PN-I-protease complexes then bind back to specific cell surface receptors where they are internalized and degraded.

PN-I is very similar, both structurally and functionally to antithrombin (AT-III). AT-III is the primary plasma inhibitor of blood coagulation. The inhibition of thrombin by AT-III in plasma is normally very weak but is accelerated significantly by the presence of heparin or by other mucopolysaccharides on the endothelial lining of blood vessels. The therapeutic value of heparin as a blood "thinning" agent is due to its enhancement of AT-III activity. Like AT-III, PN-I has a high affinity heparin binding site and inhibits thrombin much more rapidly (50-100 fold) in the presence of heparin. Thus PN-I has therapeutic potential as an anticoagulant.

On the other hand, PN-I differs from AT-III in a number of ways. Unlike AT-III, PN-I is also a good inhibitor of the fibrinolytic enzymes urokinase and plasmin, as well as trypsin. Furthermore, PN-I is not found in significant quantities in plasma and may function primarily in the tissues. The high affinity heparin binding site of PN-I serves to localize it to connective tissues and cells which contain sulfated proteoglycans on their surface and surrounding extracellular matrix. Thus PN-I's primary role seems to be in regulating proteolytic activity in tissues as opposed to blood. Further evidence for the role of PN-I is found by the fact that it is present in brain tissue and may be involved in peripheral nerve regeneration and neurite extension.

The relative efficiency with which PN-I inhibits serine proteases can be measured by the second order association rate constant ($k_{ass}$) as previously described in Bieth, J. G. (*Bull. Euro. Physiopath. Resp.* (1980) 16:183-195), and reported by Scott et al. (*J. Biol. Chem.* (1985) 260:7029-7034), both of which are incorporated herein by reference to disclose and explain the meaning of the rate association constant. In general, a value for $k_{ass}$ equal to or greater than $1 \times 10^5 M_{-1} S_{-1}$ for a particular protease-inhibitor reaction is considered to be physiologically significant (*Travis and Salveson Ann. Rev. Biochem.* (1983) 52:655-709). The $k_{ass}$ or rate association constant has inverse-mole-seconds as its units, and the larger the $k_{ass}$, the more rapid the inhibition. Accordingly, a $k_{ass}$ value is always given as a value with respect to a particular enzyme and is zero if there is no inhibition of the enzyme.

Many physiologically important protease inhibitor reactions such as elastase-alpha-1 antitrypsin and plasmin-alpha-2-antiplasmin occur with rate constants as high as $1 \times 10^7 M^{-1} S^{-1}$ or greater. The thrombin-PN-I reaction occurs at a similar high rate in the presence of heparin.

Protease nexin I (PN-I) has been purified from serum-free medium conditioned by human foreskin cells (Scott, R. W. et al., *J Biol Chem* (1983) 58:10439l0444). It is a 43 kd glycoprotein which is released by fibroblasts, myotubes, heart muscle cells, and vascular smooth muscle cells. Its release, along with that of plasminogen activator, is stimulated by phorbol esters and by mitogens (Eaton, D. L. et al., *J Cell Biol* (1983)

123:128). Native PN-1 is an approximately 400 amino acid protein containing about 10% carbohydrate. Since it is present only in trace levels in serum, it apparently functions at or near the surfaces of interstitial cells. PN-I inhibits all the known activators of urokinase proenzyme, plasmin, trypsin, thrombin, and factor Xa (Eaton, D. L. et al., *J Biol Chem* (1984) 259:6241). It also inhibits tissue plasminogen activator and urokinase. However, PN-I does not inhibit elastase.

Because the reactive site region of PN-I acts as a substrate analogue the present inventors postulated that it might be possible to drastically alter PN-I activity by modifying the reactive site sequence of PN-I, thus changing its protease specificity. Similar efforts with alpha-1-antitrypsin, for example, resulted in variants with altered and therapeutic potential (M. Courtney et al., *Nature* (1985) 313:149-151). PN-I is different from most serpins in that it is found in tissues, contains a high affinity heparin binding site which localizes it to tissues, and has a tissue clearance receptor that is responsible for endocytosis of protease-PN-I complexes. Thus the present inventor further postulated that it might be possible to generate PN-I variants as inhibitors of physiologic proteases such as elastase which, if possible, could result in molecules with very unique therapeutic potential for connective tissue diseases.

SUMMARY OF THE INVENTION

Serine proteases are proteolytic enzymes involved in a wide range of physiological activity. Serine proteases are regulated at a number of levels and their close regulation is important to maintaining proper physiological balances within living organisms. One important control for regulating serine protease activity is brought about by specific inhibitors which block proteolytic activity. An important family of such inhibitors are serine protease inhibitors or serpins which family includes protease nexin-I. The reactive site region of protease nexin-I acts as a substrate analog with respect to some protease enzymes.

The present invention involves altering the reactive site region of protease nexin-I in order to obtain a change in its protease specificity. Accordingly, the present invention provides a number of variant inhibitors of a number of physiologically important proteases. Pharmaceutical compositions comprised of excipients having the protease nexin-I variants dispersed therein are also disclosed as are methods of using these compositions to provide unique therapeutic methodologies.

In accordance with one embodiment of the invention there is provided a variant or an analog of protease nexin-I wherein the arginine residue at the $P_1$ site and/or the serine residue at the $P_1'$ site is substituted with a non-polar amino acid residue.

Yet another embodiment of the present invention provides pharmaceutical compositions which contain one or more analogs of protease nexin-I which compositions are capable of inhibiting serine proteases.

In accordance with a specific embodiment of the invention, there is provided an analog of protease nexin-I alpha as shown within FIG. 1 wherein the arginine residue at position 345 (the $P_1$ site) has been changed to a non-polar amino acid residue which is preferably a residue of valine.

In accordance with yet another specific embodiment of the invention, there is provided a protease nexin-I analog having the sequence shown within FIG. 1 wherein the serine residue at position 346 (the $P_1'$ site) is substituted with a non-polar amino acid residue which is most preferably methionine.

An important object of the present invention is to provide a range of protease nexin-I variants which alter proteolytic enzyme activity and which have different protease specificity.

Another object of the present invention is to provide pharmaceutical composition comprised of excipient carrier materials having protease nexin-I variants dispersed therein.

Another object of the present invention is to provide therapeutic methods of treatment which involves administering to a patient in need thereof a pharmaceutically effective amount of a composition comprised of excipients and protease nexin-I variants.

A feature of the present invention is that the protease nexin-I variants with different protease specificity can be produced by altering as little as a single amino acid residue within the chain of protease nexin-I.

An advantage of the present invention is that protease nexin-I variants have substantially different inhibitory effects on certain proteolytic enzymes than does protease nexin-I.

Another object of the present invention is to provide PN-I variants which are useful in treating diseases associated with plasminogen activator activity.

Yet another advantage of the present invention is to describe and disclose PN-I variants which are useful in treating elastase-related diseases.

Another feature of the present invention is that the PN-I variants have substantially altered protease specificity as compared with PN-I.

Another advantage of the present invention is that the PN-I variants have substantially greater second order association rate constants with respect to particular serine proteases as compared with the second order association rate constant of PN-I with respect to such serine proteases.

Another feature of the present invention is that the PN-I variants are heparin activatable inhibitors of elastase.

Another object of the invention is to provide variant protease inhibitors localized to the extra cellular matrix.

Yet another object of the invention is to exploit the heparin binding domain of PN-I variants and thus provide for biochemical drug delivery which localizes the PN-I variants in connective tissues.

Yet another object is to provide methods of delivery such as internasal and interpulmonary delivery which methods are carried out using pharmaceutical compositions in the form of spray formulations and aerosols.

These and other objects, advantages and features of the present invention will become apparent to those persons skilled in the art upon reading the details of the structure, formulation and usage as more fully set forth below reference being made to the accompany figures forming a part hereof.

BRIEF DESCRIPTION OF THE DRAWINGS

FIG. 1 shows the nucleotide sequence of the coding region and the deduced amino acid sequence Of PN-I alpha.

FIG. 2 shows the nucleotide sequence of the coding region and the deduced amino acid sequence of PN-I beta.

FIG. 3 is a table summarizing the kinetic properties of PN-I, PN-I alpha, PN-I beta and three variants of PN-I alpha as they affect the activity of four different enzymes.

DETAILED DESCRIPTION OF THE PREFERRED EMBODIMENT

Before the present protease nexin-I variants and formulations and methods for using such are described, it is to be understood that this invention is not limited to the particular variants, formulations or methods described as such proteins, formulations and methodologies may, of course, vary. It is to be understood that the terminology used herein is for the purpose of describing particular embodiments only, and is not intended to be limiting since the scope of the present invention will be limited only by the appended claims.

It must be noted that as used in the specification and the appended claims, the singular forms "a", "an" and "the" include plural referents unless the context clearly dictates otherwise. Thus, for example, reference to "a protease nexin-I variant" includes mixtures of such variants, reference to "an analog" includes reference to mixtures of such analogs and reference to "the method of treatment" includes reference to one or more methods of treatment of the type which will be known to those skilled in the art or will become known to them upon reading this specification, and so forth.

A. DEFINITIONS

As used herein, "protease nexin I" (PN-I) refers to a protein which is active in the standard diagnostic assays for PN-I, which are based on four criteria, as follows: (1) The protein complexes to thrombin and urokinase; (2) complexation of thrombin is accelerated by heparin; (3) the protein/protease nexin complex binds to the cell of its origin, for example to fibroblasts; and (4) heparin must inhibit this binding. The DNA codons and resulting amino acid sequences which make up PN-I alpha and PN-I beta are shown respectively in FIGS. 1 and 2.

PN-I is distinguishable from the two other protease nexin factors, PN-II and PN-III (Knauer, D. J. et al., *J Biol Chem* (1982) 257:15098–15104), which are also thrombin inhibitors, but are less strongly binding to this protease and are of different molecular weight.

"Protease nexin-I variants" and "analogs of protease nexin-I" are terms which are used synonymously herein and are intended to refer generally to proteins wherein one or more of the amino acids within protease nexin-I have been substituted with a different amino acid. More specifically, the protease nexin-I variants of the invention include substantially the same amino acid sequence as protease nexin-I but for the substitution of different amino acids at or near the reactive site. For example, substitutions of different amino acids can be made at the $P_1$, $P_2$, $P_3$ sites and/or made at the $P_{1'}$, $P_{2'}$, or $P_{3'}$ sites. Although other substitutions and deletions of amino acids in the sequence of protease nexin-I are encompassed by this invention, the substitutions at or near the reactive site are most important with respect to changing the specificity and/or reactivity of the variant with respect to particular proteases. Particularly preferred protease nexin-I variants of the invention are those which inhibit elastase and, more particularly, those which inhibit elastase and have their ability to inhibit elastase enhanced in the presence of heparin and/or heparin-like compounds. Other preferred protease nexin-I variants have increased ability to inhibit urokinase, as compared with protease nexin-I.

"Control sequence" refers to a DNA sequence or sequences which are capable, when properly ligated to a desired coding sequence, of effecting its expression in hosts compatible with such sequences. Such control sequences include at least promoters in both procaryotic and eucaryotic hosts, and preferably, transcription termination signals. Additional factors necessary or helpful in effecting expression may also be identified. As used herein, "control sequences" simply refers to whatever DNA sequence may be required to effect expression in the particular host used.

"Cells" or "cell cultures" or "recombinant host cells" or "host cells" are often used interchangeably as will be clear from the context. These terms include the immediate subject cell, and, of course, the progeny thereof. It is understood that not all progeny are exactly identical to the parental cell, due to chance mutations or differences in environment. However, such altered progeny are included in these terms, so long as the progeny retain the characteristics relevant to those conferred on the originally transformed cell. In the present case, for example, such a characteristic might be the ability to produce recombinant PN-I.

"Purified" or "pure" refers to material which is free from substances which normally accompany it as found in its native state. Thus "pure" PN-I-encoding DNA refers to DNA which is found in isolation from its native environment and free of association with DNAs encoding other proteins normally produced by cells natively producing PN-I. "Pure" PN-I refers to PN-I which does not contain materials normally associated with its in situ environment in human or other mammalian tissue. Of course, "pure" PN-I may include materials in covalent association with it, such as glycoside residues or materials introduced for, for example, formulation as a therapeutic. "Pure" simply designates a situation wherein the substance referred to is, or has been, isolated from its native environment and materials which normally accompany it.

Of course, the DNA claimed herein as purified and free of substances normally accompanying it, but encoding PN-I, can include additional sequence at the 5' and/or 3' end of the coding sequence which might result, for example, from reverse transcription of the noncoding portions of the message when the DNA is derived from a cDNA library or might include the reverse transcript for the signal sequence as well as the mature protein encoding sequence.

"Degenerate with", as referred to a DNA sequence, refers to nucleotide sequences encoding the same amino acid sequence as that referenced.

"Operably linked" refers to a juxtaposition wherein the components are configured so as to perform their usual function. Thus, control sequences or promoters operably linked to a coding sequence are capable of effecting the expression of the coding sequence.

"Heparin", "heparan sulfate" and "heparin-like compounds" are terms which are used synonymously herein. Each of the terms singly or in combination with the others is intended to encompass a large group of compounds which are generally described as sulfated polysaccharides, which includes proteoglycans and glycosaminoglycans (GAG) which are alternating copolymers of a hexosamine and an aldouronic acid. These copolymers are found in sulfated forms and are synthesized as proteoglycans and are collectively referred to as mucopolysaccharides. Other compounds such as dextran sulfate are considered "heparin-like" for purposes of the invention. Similar alternating copolymers, especially those which are highly sulfated and thus very negatively charged, are useful "heparin-like" compounds in this invention. Extensive information with respect to "heparin", "heparin-like compounds" such as glycosaminoglycans are described in detail by Benito Casu, "Structure and Biological Activity of Heparin", published in Advances in Carbohydrate Chemistry and Biochemistry, Vol. 43, pp. 51-134, which is incorporated herein by reference to disclose such compounds which might be useful in combination with certain PN-I variants disclosed herein.

A description of the invention is facilitated by listing the relationship between the one-letter symbols and the three-letter abbreviations for amino acids as follows:

| One-Letter Symbols | | Three-Letter Abbreviations |
|---|---|---|
| A | alanine | ala |
| C | cysteine | cys |
| D | aspartic acid | asp |
| E | glutamic acid | gln |
| F | phenylalanine | phe |
| G | glycine | gly |
| H | histidine | his |
| I | isoleucine | ile |
| K | lysine | lys |
| L | leucine | leu |
| M | methionine | met |
| N | asparagine | asn |
| P | proline | pro |
| Q | glutamine | gln |
| R | arginine | arg |
| S | serine | ser |
| T | threonine | thr |
| V | valine | val |
| W | tryptophan | trp |
| Y | tyrosine | tyr |

Amino acids have the following general structural formula

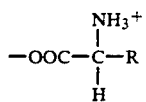

and are classified based on the chemical composition of the "R" group as follow:
1. Aliphatic
2. Hydroxyl
3. Sulfur
4. Aromatic
5. Acidic (and amides)
6. Basic
7. Imino Naturally occurring amino acids can be generally classified as being polar or non-polar as follows:

| Polar | S, T, C, Y, D, N, E, Q, R, H, K |
|---|---|
| Non-polar | G, A, V, L, I, M, F, W, P |

It is the "R" group which determines whether the amino acid will be polar or non-polar.

Amino acid residues can be generally subclassified into four major subclasses as follows:

Acidic: The residue has a negative charge due to loss of H ion at physiological pH and the residue is attracted by aqueous solution so as to seek the surface positions in the conformation of a peptide in which it is contained when the peptide is in aqueous medium at physiological pH.

Basic: The residue has a positive charge due to association with H ion at physiological pH and the residue is attracted by aqueous solution so as to seek the surface positions in the conformation of a peptide in which it is contained when the peptide is in aqueous medium at physiological pH.

Neutral/non-polar: The residues are not charged at physiological pH and the residue is repelled by aqueous solution so as to seek the inner positions in the conformation of a peptide in which it is contained when the peptide is in aqueous medium. These residues are also designated "hydrophobic" herein.

Neutral/polar: The residues are not charged at physiological pH, but the residue is attracted by aqueous solution so as to seek the outer positions in the conformation of a peptide in which it is contained when the peptide is in aqueous medium.

It is understood, of course, that in a statistical collection of individual residue molecules some molecules will be charged, and some not, and there will be an attraction for or repulsion from an aqueous medium to a greater or lesser extent. To fit the definition of "charged", a significant percentage (at least approximately 25%) of the individual molecules are charged at physiological pH. The degree of attraction or repulsion required for classification as polar or non-polar is arbitrary, and, therefore, amino acids specifically contemplated by the invention have been specifically classified as one or the other. Most amino acids not specifically named can be classified on the basis of known behavior.

Amino acid residues can be further subclassified as cyclic or noncyclic, and aromatic or nonaromatic, self-explanatory classifications with respect to the side chain substituent groups of the residues, and as small or large. The residue is considered small if it contains a total of 4 carbon atoms or less, inclusive of the carboxyl carbon. Small residues are, of course, always nonaromatic.

For the naturally occurring protein amino acids, subclassification according to the foregoing scheme is as follows:

Acidic: Aspartic acid and Glutamic acid;
Basic/noncyclic: Arginine, Lysine;
Basic/cyclic: Histidine;
Neutral/polar/small: Threonine, Serine and Cysteine;
Neutral/polar/large/nonaromatic: Threonine, Asparagine, Glutamine;
Neutral/polar/large/aromatic: Tyrosine;
Neutral/non-polar/small: Alanine;
Neutral/non-polar/large/nonaromatic: Valine, Isoleucine, Leucine, Methionine;
Neutral/non-polar/large/aromatic: Phenylalanine and Tryptophan.

The gene-encoded amino acid proline, although technically within the group neutral/non-polar/large/cyclic and nonaromatic, is a special case due to its known effects on the secondary conformation of peptide chains, and is not, therefore, included in this defined group.

Other amino acid substitutions for those encoded in the gene can also be included in peptide compounds within the scope of the invention and can be classified within this general scheme.

Variants of the invention may include commonly encountered amino acids, which are not encoded by the genetic code, for example, beta-alanine (beta-ala), or other omega-amino acids, such as 3-amino propionic, 4-amino butyric and so forth, alpha-aminoisobutyric acid (Aib), sarcosine (Sar), ornithine (Orn), citrulline (Cit), t-butylalanine (t-BuA), t-butylglycine (t-BuG), N-methylisoleucine (N-MeIle), phenylglycine (Phg), and cyclohexylalanine (Cha), norleucine (Nle), cysteic acid (Cya) and methionine sulfoxide (MSO). These also fall conveniently into particular categories.

Based on the above definition,

Sar and beta-ala are neutral/non-polar/small;

t-BuA, t-BuG, N-MeIle, Nle and Cha are neutral/-non-polar/large/nonaromatic;

Orn is basic/noncyclic;

Cya is acidic;

Cit, Acetyl Lys, and MSO are neutral/polar/large/-nonaromatic; and

Phg is neutral/non-polar/large/aromatic.

Both L and D isomers of amino acids encoded by the genetic code or otherwise are included as amino acids useful in this invention provided the resulting protein processes the required activity.

The various omega-amino acids are classified according to size as neutral/non-polar/small (beta-ala, i.e., 3-aminopropionic, 4-aminobutyric) or large (all others).

The nomenclature used to describe compounds of the present invention follows the conventional practice wherein the amino group is assumed to the left and the carboxyl group to the right of each amino acid in the peptide. In the formulas representing selected specific embodiments of the present invention, the amino- and carboxyl-terminal groups, although often not specifically shown, will be understood to be in the form they would assume at physiological pH values, unless otherwise specified. Thus, the N-terminal $H^{+}_2$ and C-terminal-$O^{-}$ physiological pH are understood to be present though not necessarily specified and shown, either in specific examples or in generic formulas.

DESCRIPTION OF PN-I (ALPHA AND BETA)

FIGS. 1 and 2, respectively, show the amino acid sequence of PN-I alpha and PN-I beta. The alpha and beta forms differ by the substitution of thr310-gly311 in PN-I beta for $arg_{310}$ in PN-I alpha. Alignment of the reactive site center of PN-I with other serpins, such as antithrombin III, predicts that arginine 345 (346 for PN-I beta) is the reactive site center or "$P_1$" site. The "$P_1$" (arginine at position 345 for PN-I alpha and 346 for PN-I beta) has been confirmed by sequencing of the peptide fragment released from PN-I upon dissociation of complexes with thrombin. Furthermore, PN-I normally inhibits only enzymes which cleave at arginine (the $P_1$ residue), such as thrombin, plasmin, trypsin, plasminogen activators, and plasma kallikrein.

Based on the above and by referring to the sequences of PN-I alpha and PN-I beta shown in FIGS. 1 and 2 respectively, it can be seen that the "$P_1'$" site is serine at position 346 for PN-I alpha and serine at position 347 for PN-I beta.

DESCRIPTION OF PROTEASE INHIBITOR ACTION

In order to allow the body to respond rapidly, many serine proteases are synthesized in their inactive proenzyme forms and are only activated during specific events. For example, coagulation is carried out when circulating proenzymes such as factor X and prothrombin are sequentially activated in response to an injury. This activation results in a cascade of clotting activity. Proteolytic activity is often localized to specific sites such as receptor binding sites. Once a proteolytic enzyme is activated, it is extremely important that the enzyme activity be confined both spatially and temporally. Such confinement is in part brought about by the inhibitory effect of serpins.

All serpins contain an inhibitor domain with a reactive peptide bond defined on either side by $P_1$ and $P_1'$ residues. The $P_1$ residue (such as arginine at position 345 for PN-I alpha and 346 for PN-I beta) is recognized by the substrate binding pocket of the target protease. Upon recognition of the "reactive" site (of the inhibitor by the protease) the protease attacks the reactive peptide bond of the inhibitor as if it were a normal substrate. However, hydrolysis of the peptide bond and release of the protease does not proceed to completion. The normal deacylation step is so slow that the reaction becomes essentially irreversible and the protease becomes trapped with the inhibitors in a stable, equal molar complex. Since the $P_1$ residue is recognized by the substrate binding pocket of the target protease, alteration of this residue can alter the protease specificity of the inhibitor entirely or substantially change the degree of the inhibitory effect obtainable.

DESCRIPTION OF PN-I VARIANTS

This invention involves the manipulation of the amino acid sequence of the PN-I, so that the reactive site is in some way altered, to change the protease specificity or the degree of inhibitory effect of PN-I on serine proteases. More specially, the present invention involves substituting one or more amino acids within protease nexin-I and/or deleting or adding amino acids to the sequence of protease nexin-I in order to obtain an effect on the reactive site of protease nexin-I so that the protease specificity of protease nexin-I and/or the degree of inhibitory effect of protease nexin-I on a serine protease is changed. In general, the change in protease specificity or degree of inhibitory effect is obtained by substituting an amino acid at the $P_1$, $P_2$, $P_3$ or, alternatively, $P_1'$, $P_2'$, $P_3'$ sites. Still more specifically, the invention involves substituting one or both of the "$P_1$" site arginine residue or "$P_1'$" site serine residue with a different residue resulting in PN-I variants with radically different protease specificities and/or inhibitory effects on particular serine proteases.

The PN-I variants of the invention can also be described in terms of their functionality. Importantly, some of the PN-I variants of the invention are capable of inhibiting elastase. Within this general group are PN-I variants wherein the ability to inhibit elastase is greatly enhanced in the presence of heparin and/or heparin-line compounds. Another group of PN-I variants of the invention include PN-I variants which have an enhanced ability to inhibit urokinase as compared with PN-I. Functional objectives of the invention, such as the production of a compounds which inhibits elastase and whose ability to inhibit elastase is enhanced in the presence of heparin, are obtained by manipulating the amino acid sequence in some manner, most importantly at the reactive site, as indicated above and described in detail below.

For purposes of clarity, substitution at a single site will be discussed first ($P_1$ site then $P_1'$ site) followed by a discussion of multiple substitutions.

"P₁" SITE SUBSTITUTIONS OF ARGININE AT POSITION 345

The arginine residue is a polar, basic amino acid. Substitution of the polar arginine with a non-polar residue has a dramatic effect on the degree of serine protease inhibition obtainable. As a specific example of this effect, reference is made to Example 3 wherein arginine (at position 345 for alpha, 346 for beta) is substituted with valine. As shown in FIG. 3, the $Val_{345}$ variant (i.e., valine has been substituted for arginine a position 345 of PN-I alpha) essentially eliminates thrombin inhibitory activity with or without heparin. At the same time, the $Val_{345}$ variant is a good inhibitor of neutrophil elastase activity. This is surprising when it is noted that native fibroblast PN-I has no inhibitory effect on elastase.

FIG. 3 can be understood by knowing that the relative efficiency at which protease inhibitors (such as the PN-I variants of the invention) inhibit serine proteases are measured by a known standard. That standard is the second order association rate constant ($k_{ass}$) as described in (Bieth, J. G., *Bull. Euro. Physiopath. Resp.* (1980) 16:183–195) and reported by Scott et al. (*J. Biol. Chem.* (1985) 260:7029–7034), both of which are incorporated herein by reference to disclose second order association rate constants.

In general, a value for $k_{ass}$ equal to or greater than $1\times10^5\ M_{-1}S_{-1}$ for a particular protease-inhibitor reaction is considered to be physiologically significant (*Travis and Salveson Ann. Rev. Biochem.* (1983) 52:655–709), incorporated herein by reference to describe the significance of rate constants. Many physiologically important protease-inhibitor reactions such as elastase-alpha-1-antitrypsin and plasmin-alpha-2-antiplasmin occur with rate constants as high as $1\times10^7\ M_{-1}S_{-1}$ or greater. The thrombin-PN-I reaction occurs at a similar high rate in the presence of heparin.

From FIG. 3, it can be seen that PN-I has essentially no effect with respect to inhibiting the activity of elastase. However, the alpha $Val_{345}$ or beta $Val_{346}$ variants of the present invention clearly provide not just a new biological activity for the serpin, i.e., its ability to inhibit elastase, but clearly provide an extremely potent elastase inhibitor. The ability of the alpha $Val_{345}$ or beta $Val_{346}$ variants to inhibit elastase to such a degree was in itself a surprising finding. However, it was clearly unexpected to find that in addition to providing such a potent elastase inhibitor that these variants had still further increased potency with respect to inhibiting elastase while in the presence of heparin.

The PN-I variants of the invention are clearly capable of providing not only improved potency with respect to acting as elastase inhibitors, but are capable of providing such activity site specifically in that their activity is greatly enhanced in the presence of heparin, heparin-like compounds or other related mucopolysaccharides normally found in the endothelial lining of blood vessels. In addition to heparin, a range of sulfated proteoglycans such as heparin and other heparin-like compounds normally found on the surface and surrounding extracellular matrix would provide not only increased potency with respect to the ability of the variants of the invention to inhibit elastase but provide site-specific activity due to the affinity of these variants to heparin and heparin-like compounds.

The inhibitory effect of the alpha $Val_{345}$ or beta $Val_{346}$ variant on elastase is increased approximately two orders of magnitude in the presence of heparin. It can be readily determined that "$P_1$" variants with non-polar residues such as valine substituted for the polar arginine residue could be used as a heparin activatable inhibitor in order to treat individuals suffering from elastase-related diseases such as emphysema, congenital alpha-I-antitrypsin deficiency, inflammation and septic shock. Non-polar residues which can be used include G, A, V, L, I, M, F, W and P, and more preferably (due to "R" group structures similar to valine) G, A, V, L and I and most preferably V.

In a broad sense, the present invention encompasses PN-I variants which are capable of acting as potent elastase inhibitors. More specifically, the invention encompasses such PN-I variants which act as elastase inhibitors and further wherein the ability to inhibit elastase is greatly increased in the presence of heparin and heparin-like materials. Still more specifically, the invention encompasses PN-I variants which act as elastase inhibitors and which variants have their ability to inhibit elastase increased 10 fold or more in the presence of heparin, preferably 50 fold or more in the presence of heparin and more preferably 100 fold or more in the presence of heparin. Useful formulations of the invention include PN-I variants formulated in pharmaceutical compositions along with heparin and heparin-like compounds such as various sulfated polysaccharides or proteoglycans. It is particularly preferred if the heparin-like compounds are highly sulfated, thus providing high negative charges.

Above it has been pointed out that $P_1$ variants of the invention which include non-polar residues such as valine substituted for the polar arginine can be used to treat individuals due to the ability of these $P_1$ variants to inhibit the activity of elastase. This is quite surprising since other proteases such as urokinase and plasmin which are inhibited by PN-I are not heparin activatable. While not wishing to be bound by any particular theory, it may be that the $P_1$ variants of the present invention are effective in inhibiting elastase due to the cationicity of elastase which promotes its binding to heparin which is anionic. Accordingly, in order to obtain other PN-I variants which are heparin activatable inhibitors of elastase, the active site should be substituted with other residues which are non-polar and have similar "R" groups in order to have a reasonable expectation of similar activity.

"$P_1'$" Site Substitutions

The serine residue is a polar neutral amino acid wherein the "R" group is $-CH_2OH$. Substitution of the polar serine with a non-polar residue has a dramatic effect on the degree of serine protease inhibition obtainable. As a specific example of this effect, reference is made to Example 1 wherein serine is substituted with methionine. As shown in FIG. 3, the PN-$Met_{346}$ variant (i.e., methionine has been substituted for serine at position 346 of PN-I alpha) has decreased inhibitory activity against thrombin and increased inhibitory activity against tissue-type plasminogen activator (tPA).

In that tPA is a fibrinolytic enzyme, the $P_1'$ variants such as PN-$Met_{346}$ could be used therapeutically to treat conditions involving fibrinolytic activity. Such conditions include cancer, hemorrhaging, inflammation, such as, but not limited to, skin inflammation.

In Example 2, a $P_1'$ mutant was prepared wherein the serine residue at position 346 was substituted with threonine which, like serine, is a polar residue. As shown within FIG. 3, the PN-$Thr_{346}$ variant did not have substantially changed activity as compared with PN-I. Accordingly, it was concluded that the substitution of the polar serine residue with non-polar residues resulted in substantial changes in the activity and/or specificity of the inhibitor whereas substitution of the polar serine residue with other polar residues did not have a substantial effect on the specificity and/or activity of the inhibitor.

Based on the above, it can be readily determined that $P_1'$ variants with non-polar residues such as methionine substituted for the polar serine residue could be used to treat diseases and normal processes associated with plasminogen activator activity. Diseases which might be regulated by such a PN-I variant include cancer, hemorrhaging, inflammation, including, but not limited to, skin inflammatory diseases. Non-polar residues which can be used include G, A, V, L, I, M, F, W, and P, and more preferably include (due to "R" group structures similar to methionine) V, I, L, and M and most preferably M.

The creation of other PN-I variants by substituting the above-suggested non-polar residues for the polar serine residue would be likely to provide similar results, i.e., have traumatic effects on target proteases. Of particular interest are inhibitors of chymotrypsin which are created by replacing the active site polar serine residue with phenylalanine. In addition, it might be possible to obtain a PN-I variant which inhibits chymotrypsin by replacing the serine residue with tyrosine which is a polar residue having a substantially different "R" group structure from the —OH "R" group structure of serine.

DOUBLE SUBSTITUTION AT $P_1$ AND $P_1'$ SITES

The sequence of PN-I α and PN-I β are given in FIGS. 1 and 2 respectively. Further, factors describing the characteristics of both have been put forth above. Prior to the present disclosure, variants of the invention such as elastase inhibitors of any PN-I were not known. Further, it was not known whether any such variants would provide any activity, let alone the type of activity obtained. The present invention not only provides variants wherein active sites have been replaced, but shows that such variants have activity and that the activity is substantially different from the activity of the original PN-I. Now that a number of variants and their activity have been shown, it can be seen that still other variants which might possess activity can also be produced. In connection therewith, it is postulated that variants can be produced wherein substitution is made at both the $P_1$ and $P_1'$ sites. Such double substitutions could be put forth in a variety of different ways.

One approach to producing such variants is to substitute one of the sites with a residue which is substantially different from the residue present such as including a non-polar resin in place of a polar resin while substituting the other site with a residue which is substantially similar to the residue present there both in terms of being polar or non-polar and in terms of having a similar "R" group. Another approach is to substitute both sites with residues which are substantially different from the original residues. Yet another possible means for producing variants would be to use either of the above-suggested strategies in combination with substituting other sites. A variety of such substitutions will occur to those skilled in the art upon reading this disclosure. What is important is that the resulting variant continued to provide activity. The ability of the variant to provide activity will depend on the substrate specificity. Accordingly, the present invention is intended to encompass single, double and multiple substitutions of the residues to provide variants which continue to have activity with respect to a given substrate.

In connection with the present invention, the PN-I variants which have activity are variants which have (1) substantially increased potency with respect to inhibiting tPA or urokinase; (2) substantially increased potency with respect to inhibiting elastase; or most preferably (3) substantially increased potency with respect to inhibiting elastase and which potency is still further increased dramatically in the presence of heparin. In that the present invention has demonstrated that it is possible to produce PN-I variants which inhibit elastase and has further demonstrated that it is possible to produce such variants which not only inhibit elastase, but have substantially increased potency to inhibit elastase in the presence of heparin others skilled in the art of such inhibitors will be able to deduce other variants which are intended to be within the scope of the present invention.

USE AND ADMINISTRATION

The different PN-I variants of the invention (as indicated above) can provide different effects. For example, $P_1$ variants with non-polar residues such as valine substituted for the polar arginine residue could be used as heparin activatable inhibitors. Such inhibitors could be used to treat individual suffering from elastase-related diseases. Although not limited to such diseases, such variants could be used to treat emphysema, congenital alpha-1-antitrypsin deficiency, inflammation, arthritis and septic shock.

One of the most important and immediate perceived uses of the PN-I variants of the invention would be to include such variants within various topical formulations such as creams or gels and a combination of such formulations with various bandages in order to be applied to wounds in order to aid in wound healing and decrease inflammation of wound sites. In that PN-I variants of the invention are believed to be effective in decreasing inflammation, injectable formulations containing the PN-I variants of the invention could be injected directly into inflamed joints or other inflamed areas of the body in order to decrease the inflammation. Further the formulations of the invention could be used prophylactically by providing the PN-I variants to a particular site which may be expected to be subjected to trauma (and thus inflammation) in order to prevent the inflammation from occurring originally.

It is generally not possible to obtain desirable results by administering large protein compounds such as protease nexin-I and its variants by oral delivery systems. Such proteins are generally digested in the GI tract (unless formulated with special carriers) and do not enter the cardiovascular system in their original forms due to such digestion. Such protein materials can be administered by any type of injections such as intramuscularly or intravenously, thus avoiding the GI tract. Other modes of administration include transdermal and transmucosal administrations provided by patches and/or topical cream compositions. Transmucosal administrations and include nasal spray formulations which include the protease nexin-I variant within a nasal formulation which contacts the nasal membranes and diffuses through those membranes directly into the cardiovascular system. Formulations which include the PN-I variants within aerosols for intrapulmonary delivery are also contemplated by this invention as is intraocular delivery systems wherein the PN-I variants are included within ophthalmic formulations for delivery in the form of eye drops.

Any of the above suggested means of administration could be provided in a variety of different formulations. The formulations can be designed to provide the PN-I variants systemically or to a particular site. Further, the formulations can be designed so as to provide the PN-I variants as quickly as possible or in a sustained release or timed released manner. For example, topical formulations could be created whereby the PN-I variants of the invention were incorporated or disbursed throughout topical polymer formulations capable of slowly releasing the PN-I variants to a wound site in order to continually aid in wound healing and continually aid in preventing inflammation.

As indicated above, different formulations of the invention can be administered in a variety of different manners in order to introduce the PN-I variants into the cardiovascular system. The PN-I-variants are administered for a variety of different purposes, all of which relate generally to blocking proteolytic activity. Intravenous formulations containing the PN-I variants are particularly useful for their antithrombolytic effect and therefore can be administered to aid in the prevention and/or alleviation of strokes and/or heart attacks.

It is pointed out that PN-I is not found in significant quantities in plasma and may function primarily in tissues. The high affinity heparin binding site of PN-I appears to serve to localize PN-I to connective tissues and cells which contain sulfated proteoglycans on their surface and surrounding extracellular matrix. Thus, the primary role of PN-I seems to be in regulating proteolytic activity in tissues as opposed to blood. In that PN-I is found in brain tissue another aspect of the invention involves delivering formulations of the invention containing PN-I variants in order to facilitate peripheral nerve regeneration.

EXAMPLES

The following examples are provided so as to give those of ordinary skill in the art a complete disclosure and description of how to make and use the PN-I variants of the invention and are not intended to limit the scope of what the inventors regard as their invention. Efforts have been made to insure accuracy with respect to the specifics given such as the association rate constants and temperature but some experimental errors and deviations should be accounted for. With respect to the formulation examples, parts are parts by weight, and any temperature readings are in degrees centigrade and all experiments were carried out at or near atmospheric pressure.

EXAMPLE A

The Synthesis of PN-I

PN-I was purified to homogeneity from serum-free medium conditioned by human foreskin fibroblasts in microcarrier cultures by affinity chromatography on heparin-agarose, followed by gel exclusion chromatography, as described in detail by Scott, R. W. et al., *J Biol Chem* (1985) 260:7029–7034, incorporated herein by reference. Of course, other chromatographic supports which contain heparin for affinity binding can also be used. The purified protein shows an $M_r$ of 42–43 kd, based on sedimentation equilibrium analysis, or of 47 kd, estimated from gel-exclusion chromatography. The purified material shows the properties exhibited by PN-I when contained in conditioned medium, including formation of sodium dodecylsulfate-stable complexes with thrombin, urokinase, and plasmin; inhibition of protease activity; heparin-enhanced inhibition of thrombin; and cellular binding of protease-PN complexes in a heparin-sensitive reaction. The N-terminal amino acid sequence of the isolated, purified protease nexin was determined for the first 34 amino acids to be: Ser-His-Phe-Asn-Pro-Leu-Ser-Leu-Glu-Glu-Leu-Gly-Ser-Asn-Thr-Gly-Ile-Gln-Val-Phe-Asn-Gln-Ile-Val-Lys-Ser-Arg-Pro-His-Asp-Asn-Ile-Val-Ile.

The PN-I variants of the present invention can be synthesized by utilizing the pure PN-I which has been isolated and purified in the manner indicated above. The variants can be obtained by cleaving the purified PN-I protein at the $P_1$ or $P_1'$ site and replacing the arginine, serine or both residues at that site with the desired non-polar substitute residue. After replacement of the desired residue with the desired non-polar residue, the segments can be fused utilizing protocols known to those skilled in the art. Although such methodology could be utilized in order to obtain the variants of the present invention, this methodology is somewhat cumbersome and is extremely limited, due to the very small amounts of PN-I which can be extracted and purified. Accordingly, although the above procedure could be utilized, it is not the preferred method of making PN-I or the variants disclosed herein. PN-I and its variants are generally produced utilizing recombinant technology, as described below.

EXAMPLE B

A Generalized Recombinant Synthesis of PN-I

Methods of producing protease nexin-I utilizing recombinant technology are disclosed within published European patent application 873049126 which published application is incorporated herein by reference to disclose recombinant technologies utilized in producing protease nexin-I. The procedure can be modified by those skilled in the art, reading this disclosure, to obtain PN-I variants.

cDNA encoding the complete human PN-I protein was obtained from a foreskin fibroblast DNA library. The retrieval of this clone took advantage of probes based on the amino acid sequence determined in the native protein. The cloned cDNA is amenable to expression in recombinant cells of both procaryotic and eucaryotic organisms by excising the coding sequence from the carrier vector and ligating it into suitable expression systems.

The PN-I can be directly produced as a mature protein preceded by a Met N-terminal amino acid (which may or may not be processed, depending on the choice of expression systems) may be produced as a fusion protein to any desirable additional N-terminal or C-terminal sequence, or may be secreted as a mature protein when preceded by a signal sequence, either its own, or a heterologous sequence provided by, for example, the known signal sequence associated with the bacterial-lactamase gene or with secreted human genes such as insulin or growth hormones. Means for providing suitable restriction sites at appropriate locations with respect to the desired coding sequence by site-directed mutagenesis are well understood, and the coding sequence can thus be provided with suitable sites for attachment to signal sequence or fusion sequence, or into expression vectors.

If bacterial hosts are chosen, it is likely that the protein will be produced in nonglycosylated form. If the PN-1 is produced intracellularly as a "mature" protein, the N-terminal methionine may be only partially processed, or not processed at all. Thus, the protein produced may include the N-terminal met. Modification of the protein produced either intracellularly or as secreted from such bacterial host can be done by providing the polysaccharide substances, by refolding using techniques to sever and reform disulfide bonds, or other post-translational ex vivo processing techniques. If the protein is produced in mammalian or other eucaryotic hosts, the cellular environment is such that post-translational processing can occur in vivo, and a glycosylated form of the protein is produced.

The recombinant cells are cultured under conditions suitable for the host in question, and the protein is recovered from the cellular lysate or from the medium, as determined by mode of expression. Purification of the protein can be achieved using methods similar to that disclosed by Scott, R. W. et al., *J Biol Chem* (supra), or by other means known in the art.

Once DNA segments coding for the production of PN-I have been inserted into bacterial hosts, multiple copies of the segments can, of course, be cloned by growing the bacteria. The segments can be extracted from the bacteria by the use of conventional methodology whereby the DNA is extracted by subjecting disrupted cells to centrifugation and then subjecting the extracted DNA to enzyme digestion, which will result in obtaining the desired segments by subjecting the digested DNA to separation processes such as gel electrophoresis and blotting. The segments coding for the production of PN-I can then be subjected to conventional recombinant methodologies in order to substitute codons coding for the arginine and/or serine with new codons which code for the production of the desired non-polar amino acid residue. Once such recombinant segments are produced, they can be reinserted into vectors and hosts in the manner described above in order to obtain the production of the desired PN-I variants. A variety of vector and host systems known to those skilled in the art can be used.

In addition, it is pointed out that PN-I variants might be made by using recombinantly produced PN-I and then substituting only the desired "R" group (e.g., —OH of serine 346) with a non-polar "R" group (e.g., —$CH_2CH_2$-s-$CH_3$) to get a PN-Met$_{346}$ variant. Such replacements of the "R" group can be carried out using published protocols known to those skilled in the art.

EXAMPLE C

Production of recombinant PN-I variants in insect cells using a baculovirus expression system C.1. Construction of plasmid expression vector In order to produce PN-I and/or PN-I variants in insect cells, the cDNA sequence must first be inserted into a suitable plasmid expression vector, such as pAC373. Appropriate restriction sites for this insertion can be created by standard site-directed mutagenesis procedures. The essential properties of a suitable expression vector include a transcriptional promoter such as the polyhedron gene promoter of pAC373, and flanking homologous sequences to direct recombination into the baculovirus genome. A polyadenylation signal, such as the one from the polyhedron gene present in this plasmid vector, may or may not be necessary for expression of the recombinant gene. A marker gene such as the beta-galactosidase gene of *E. coli*, juxtaposed to regulatory sequences including a transcriptional promoter and possibly a polyadenylation signal, may be included in the vector but is not essential for expression of a convected gene.

C.2. Creation of recombinant baculovirus

A chimeric baculovirus is created by homologous recombination between the expression plasmid containing the PN-I target gene and wild type baculovirus DNA. Plasmid and wild type baculovirus DNA are co-precipitated by the calcium phosphate technique and added to uninfected Spodoptera frugiperda (Sf9) insect cells. Four to seven days following transfection, cells will exhibit a cytopathic morphology and contain the nuclear occlusion bodies typically produced by viral infection. The cell-free culture media containing both wild type and recombinant virus is harvested.

C.3. Identification and isolation of chimeric baculovirus

Clonal isolates of virus can be obtained from this co-transfection stock by plaque purification on Sf9 cell monolayers overlaid with agarose. Candidate plaques for analysis will be identified by a plaque morphology negative for occlusion bodies. If the expression plasmid contains a marker gene such as beta galactosidase, recombinant plaques will be indicated by the blue color produced from a chromogenic substrate such as 5-bromo-4-chloryl-3-indolyl-b-D-galactopyranoside (X-gal) in the agarose plating medium. Picked plaques will be used for inoculation of cells in multiwell dishes. The resulting cell lysates and infected cell supernatants can be evaluated for expression of recombinant PN-I, using standard activity or immunological assays. Positive wells may require additional rounds of plaque purification to obtain pure recombinant virus stocks free from wild type contamination.

C.4. Batch production of PN-I

Sf9 cells are adapted to growth in serum-free, low protein medium such as ExCell (J. R. Scientific). Cells are collected from suspension culture by gentle centrifugation and resuspended in fresh medium containing the viral inoculum at a concentration of ten million cells per ml., using a multiplicity of infection of one virus plaque forming unit per cell. After a period of two hours, the culture is diluted five fold with fresh medium and incubated two to three days. At the end of that time, the cells are pelleted by centrifugation and the conditioned medium harvested. PN-I is purified from the cell-free supernatant by standard means.

Variants of PN-I may be created and produced in the same manner as described above.

C.5. Characterization of insect cell derived PN-I

PN-I produced in insect cells using a baculovirus expression system is a glycosylated protein of approximate molecular weight of 42,000 kd. The N-terminal amino acid sequence is identical to that of mature mammalian cell PN-I, indicating correct processing of the signal sequence. The specific activity vs thrombin and association kinetics, including rate enhancement effect of heparin, are indistinguishable from authentic PN-I.

EXAMPLES OF THE ACTIVITY OF ACTUAL VARIANTS OF THE INVENTION

As described above, the target specificity of serpins is in part determined by the amino acid sequence of the reactive site. The following examples describe three different mutation of the native PN-I alpha gene encoding altered sequences the reactive site. All three variant PN-I molecules have been expressed in tissue culture and purified in milligram amounts. In the first of these, the serine residue at position 346 has been changed to a methionine (Met$_{346}$) In the second, the serine at 346 has been changed to a threonine (Thr$_{346}$). In the third, arg$_{345}$ has been changed to a valine (Val$_{345}$). A summary of the kinetic properties of these variants is shown in Table I.

EXAMPLE 1

PN-Met$_{346}$ is an improved inhibitor of tPA. The association rate constant of this variant vs tPA is $8.5\times10^4$ $M_{-1}S_{-1}$ compared to $3.2\times10^4$ $M_{-1}S_{-1}$ for native PN-I. The properties of PN-Val$_{345}$ are dramatically altered. This variant is a strong inhibitor of elastase ($k_{ass}=6\times10^5$ $M_{-1}S_{-1}$). In addition, this inhibition is enhanced by at lease two orders of magnitude in the presence of heparin with a $k_{ass}$ greater than $6\times10^7$ $M_{-1}S_{-1}$. Thus, it can be seen that this molecule is a unique, heparin activatable inhibitor of elastase.

PN-Met$_{346}$ and Uses

The activity of this mutant is decreased against thrombin and increased against the fibrinolytic enzyme tissue-type plasminogen activator. The uses for this variant are in therapeutic conditions where fibrinolytic activity is involved. For example, fibrinolysis, tissue remodeling, cell invasion, and neurite outgrowth. Diseases and normal processes associated with plasminogen activator activity which might be regulated by this variant include cancer, hemorrhaging, inflammation, skin inflammatory diseases, mammary gland involution, ovulation, trophoblast implantation, angiogenesis, and neurite outgrowth.

EXAMPLE 2

PN-Thr$_{346}$

The activity of this mutant does not appear to be significantly changed.

EXAMPLE 3

PN-Val$_{345}$

The activity of this variant is drastically altered with a total loss of thrombin inhibitory activity. On the other hand, this molecule is a good inhibitor of neutrophil elastase in the absence of heparin and is accelerated in its inhibition of elastase by about 100 fold in the presence of heparin. This variant could be used as a heparin activatable inhibitor in such elastase-related diseases as emphysema, congenital alpha-1-antitrypsin deficiency, inflammation, and septic shock. Since elastase is known to cleave and inactivate a large number of serpins including AT-III and PN-1, the PN-Val$_{345}$ variant could also be used to increase the levels of other serpins (such as PN-I and AT-III) by effectively inhibiting elastase. The heparin binding site could be exploited by either cotherapy with heparin, dextran sulfate (or other heparin-like mucopolysaccharides) or by delivery of PN-Val$_{345}$ directly to connective tissue where it would be immobilized by localized sulfated proteoglycans.

The PN-I variants of Examples 1, 2 and 3 are shown below as compared with native PN-I at the active site.

NATIVE PN-I

| | | | | | | | | | | | | |
|---|---|---|---|---|---|---|---|---|---|---|---|---|
| | | | | | | P1 | P1' | | | | | |
| A.A. | 340 | | | | | 345 | | | | | 350 | |
| | Ala | Ile | Leu | Ile | Ala | <u>Arg</u> | <u>Ser</u> | Ser | Pro | Pro | Trp | Phe |
| | GCA | ATT | CTC | ATT | GCA | <u>AGA</u> | <u>TCA</u> | TCG | CCT | CCC | TGG | TTT |

1) SER—MET 346 (NlaIII site)
PAI-1 like tPA inhibitor
ARG MET
CGC ATG

2) SER—THR 346 (AatII site)
PAI-2 like UK inhibitor
ARG THR
CGG ACG TC

3) ARG—VAL 345 (HphI site)
like a1 antitrypsin (Val)
ALA VAL SER
GCG GTG AGT

While the present invention has been described with reference to specific protease nexin-I variants and formulations containing such, it should be understood by those skilled in the art that various changes may be made and equivalence may be substituted without departing from the true spirit and scope of the invention. In addition, many modifications may be made to adapt a particular situation, material, excipient, PN-I variant, process, process step or steps to the objective, spirit and scope of the invention. All such modifications are intended to be within the scope of the claims appended hereto.

What is claimed is:

1. A protease nexin-I variant capable of inhibiting elastase, where said variant is comprised of non-polar amino acid substitutions at the substrate binding site.

2. A protease nexin-I variant as claimed in claim 1, wherein the rate association constant of the variant with respect to elastase is at least $5.0 \times 10^5 \, M^{-1}S^{-1}$.

3. A protease nexin-I variant as claimed in claim 2, wherein the rate association constant of the variant with respect to elastase is increased 10 times or more when the variant is in the presence of heparin or a heparin-like compound.

4. A protease nexin-I variant as claimed in claim 3, wherein the rate association constant of the variant with respect to elastase is increased 50 times or more when the variant is in the presence of heparin or a heparin-like compound.

* * * * *